US008026058B2

(12) United States Patent
Ankenbauer et al.

(10) Patent No.: US 8,026,058 B2
(45) Date of Patent: Sep. 27, 2011

(54) PCR HOT START BY MAGNESIUM SEQUESTRATION

(75) Inventors: Waltraud Ankenbauer, Penzberg (DE); Dieter Heindl, Paehl (DE); Frank Laue, Paehl-Fischen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/198,966

(22) Filed: Aug. 27, 2008

(65) Prior Publication Data

US 2010/0285535 A1    Nov. 11, 2010

Related U.S. Application Data

(63) Continuation of application No. PCT/EP2007/001585, filed on Feb. 23, 2007.

(30) Foreign Application Priority Data

Feb. 27, 2006 (EP) ..................................... 06003903

(51) Int. Cl.
*C12Q 1/68* (2006.01)
*C12P 19/34* (2006.01)
*C07K 5/04* (2006.01)
*C07K 7/06* (2006.01)
*C07K 7/08* (2006.01)

(52) U.S. Cl. ........... 435/6; 435/91.2; 530/327; 530/328; 530/330

(58) Field of Classification Search ........................ None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 4,965,188 A | 10/1990 | Mullis et al. | |
| 5,118,801 A | 6/1992 | Lizardi et al. | |
| 5,210,015 A | 5/1993 | Gelfand et al. | |
| 5,338,671 A | 8/1994 | Scalice et al. | |
| 5,411,876 A | 5/1995 | Bloch et al. | |
| 5,449,603 A | 9/1995 | Nielson et al. | |
| 5,487,972 A | 1/1996 | Gelfand et al. | |
| 5,538,848 A | 7/1996 | Livak et al. | |
| 5,677,152 A | 10/1997 | Birch et al. | |
| 5,693,502 A | 12/1997 | Gold et al. | |
| 5,773,258 A | 6/1998 | Birch et al. | |
| 5,792,607 A | 8/1998 | Backman et al. | |
| 5,804,375 A | 9/1998 | Gelfand et al. | |
| 5,985,619 A | 11/1999 | Sutherland et al. | |
| 6,020,130 A | 2/2000 | Gold et al. | |
| 6,174,670 B1 | 1/2001 | Wittwer et al. | |
| 6,241,557 B1 | 6/2001 | Reichardt | |
| 6,391,551 B1 | 5/2002 | Shultz et al. | |
| 6,403,341 B1 | 6/2002 | Barnes et al. | |
| 6,617,114 B1 * | 9/2003 | Fowlkes et al. ................. 506/10 |
| 6,667,165 B2 | 12/2003 | Peters | |
| 6,746,104 B2 * | 6/2004 | Ellson et al. ..................... 506/30 |

FOREIGN PATENT DOCUMENTS

| | | |
|---|---|---|
| EP | 0744470 | 11/1996 |
| EP | 0799888 | 10/1997 |
| EP | 0930370 | 7/1999 |
| EP | 1275735 | 1/2003 |
| GB | 2293238 | 3/1996 |
| WO | 97/46706 | 12/1997 |
| WO | 97/46707 | 12/1997 |
| WO | 97/46712 | 12/1997 |
| WO | 97/46714 | 12/1997 |
| WO | 99/46400 | 9/1999 |
| WO | 00/68411 | 11/2000 |
| WO | 02/14555 | 2/2002 |

OTHER PUBLICATIONS

Shigematsu et al. Fine Specificity of T Cells Reactive to Human PDC-E2 163-176 Peptide, the Immunodominant Autoantigen in Primary Biliary Cirrhosis: Implications for Molecular Mimicry and Cross-Recognition Among Mitochondrial Autoantigens. Hepatology (2000) 32: 901-909.*
Woollard et al. Synthetic peptides induce antibody against a host-protective antigen of *Echinococcus granulosus*. Vaccine (2000) 18: 785-794.*
Lee et al. Control of Metal Coordination Number in de Novo Designed Peptides through Subtle Sequence Modifications. Journal of the American Chemistry Society (2004) 126: 9178-9179.*
Jackson et al. Inherited mutations within the calcium-binding sites of the integrin orllb subunit (platelet glycoprotein llb): Effects of the amino acid side chain and the amino acid position on cation binding. European Journal of Biochemistry (1996) 240: 280-287.*
Bernard et al, Integrated Amplication and Detection of the C677T Point Mutation in the Methylenetetrahydrofolate Reductiase Gene by Fluorescence Resonance Energy Transfer and Probe Melting Curves, Analytical Biochemistry, 255:101-107 (1998).
Chakrabarti et al, The Enhancement of PCT Amplification by Low Moledular Weight Amides, Nucleic Acids Research, 29(11): 2377-2381, Oxford University Press (2001).
Chou et al, Prevention of Pre-PCR Mis-Priming and Primer Dimerization Improves Low-copy-number Amplifications, Nucleic Acids Research 20(7):1717-1723, Oxford University Press (1992).
Fields et al, Solid Phase Peptide Synthesis Utilizing 9-fluorenylmethoxycarbonyl Amino Acids, Int. J. Peptide Protein Res. 35:161-214 (1990).
Hengen, Methods and Reagents, Trends in Biochemical Science 22:225-226, Elsevier Science Ltd. (1997).
Hildebrand et al, Action of Heparin on Mammalian Nuclei, Biochemica et Biophysica Acta 477:295-311 (1977).
Kaboev et al, Hot Start of the Polymerase Chain Reaction Using DNA Helicases, Biiorg Khim 25:398-400 (1999).
Kainz et al, Specificity-Enhanced Hot-Start PCR: Addition of Double-Stranded DNA Fragments Adapted to the Annealing Temperature, BioTechniques 28(2):278-282 (2000).

(Continued)

*Primary Examiner* — Young J Kim
*Assistant Examiner* — Angela M Bertagna

(57) ABSTRACT

The present invention is directed to a synthetic peptide having a length of not more than 30 amino acids comprising a divalent cation binding site. Such a peptide according to the present invention is part of a composition for nucleic acid amplification and provides for a so-called hot start effect.

8 Claims, 7 Drawing Sheets

OTHER PUBLICATIONS

Kellogg et al, TaqStart Antibody: "Hot Start" PCR Facilitated by a Neutralizing Monoclonal Antibody Directed Against Taq DNA Polymerase, Biotechniques 16:1134-1137 (1994).

Lin et al, Inhibition of Multiple Thermostable DNA Polymerases by a Heterodimeric Aptamer, J. Mol. Biol. 271:100-111 (1997).

Matthews et al, Analytical Strategies for the Use of DNA Probes, Analytical Biochemistry 169:1-25 (1988).

Moretti et al, Enhancement of PCT Amplification Yield and Specificity Using AmpliTaq Gold DNA Polymerase, BioTechniques 25:716-722 (1998).

Nilsson et al, Heat-Mediated Activiation of Affinity-Immobilized Taq DNA Polymerase, BioTechniques 22:744-751 (1997).

Sharkey et al, Antibodies as Thermolabile Switches: High Temperature Triggering for the Polymerase Chain Reaction, Biotechnology (NY) 12:506-509 (1994).

Sturzenbaum, Transfer RNA Reduces the Formation of Primer Artifacts During Quantitative PCR, BioTechniques 27:50-52 (1999).

Cierniewski et al, Characterization of Cation-Binding Sequences in the Platelet Integrin GPIIb-IIIa by Terbium Luminescence, Biochemistry 33:12238-12246 (1994).

Xu et al, Structural and ICAM-1-Docking Properties of a Cyclic Peptide From the I-domain of LFA-1: An Inhibitor of ICAM-1/LFA-1-Mediated T-Cell Adhesion, Biomol. Struct. Dyn. 19:789-799 (1993).

Zhao et al, Gas-Phase Fragmentations of Anionic Complexes Between Peptides and Alkaline Earth Metal Ions: Structure-Specific Side-Chain Interactions, J. Am. Chem. Soc. 115:2854-2863 (1993).

Shigematsu et al, Fine Specificity of T Cells Reactive to Human PDC-E2 163-176 Peptide, the Immunodominant Autoantigen in Primary Biliary Cirrhosis: Implications for Molecular Mimicry and Cross-Recognition Among Mitochondrial Autoantigens, Hepatology 32: 901-909 (2000).

Jackson et al, Inherited Mutations Within the Calcium-Binding Sites of the Integrin allb Subunit (platelet glycoprotein llb), Europ. J. of Biochem. 240:280-287 (1996).

Woollard et al, Synthetic Peptides Induce Antibody Against a Host-Protective Antigen of Echinococcus Granulosus, Vaccine 18:785-794 (2000).

Lee et al, Control of Metal Coordination Number in de Novo Designed Peptides Through Subtle Sequence Modifications, J. Am. Chem. Soc. 126:9178-9179 (2004).

* cited by examiner

PCR HOT START BY MAGNESIUM SEQUESTRATION

RELATED APPLICATIONS

This application is a continuation of PCT/EP2007/001585 filed Feb. 23, 2007 and claims priority to EP 06003903.9 filed Feb. 27, 2006.

FIELD OF THE INVENTION

The present invention relates to the technical field of amplification of nucleic acids by means of performing the polymerase chain reaction process (PCR). More precisely, the present invention provides a new hot start alternative for performing PCR, which prevents unspecific priming events and the generation of false amplification products.

BACKGROUND

A major problem with nucleic acid amplification and more especially with PCR is the generation of unspecific amplification products. In many cases, this is due to an unspecific oligonucleotide priming and subsequent primer extension event prior to the actual thermocycling procedure itself, since thermostable DNA polymerases are also moderately active at ambient temperature. For example, amplification products due to eventually by chance occurring primer dimerization and subsequent extension are observed frequently. In order to overcome this problem, it is well known in the art to perform a so called "hot start" PCR, wherein one component essential for the amplification reaction is either separated from the reaction mixture or kept in an inactive state until the temperature of the reaction mixture is being raised for the first time. Since the polymerase cannot function under these conditions, there is no primer elongation during the period when the primers can bind none specifically. In order to achieve this effect, several methods have been applied:

Physical Separation of the DNA Polymerase

The physical separation can be obtained for example by a barrier of solid wax, which separates the compartment containing the DNA polymerase from the compartment containing the bulk of the other reagents. During the first heating step the wax is then melting automatically and the fluid compartments are mixed (Chou, Q., et al., Nucleic Acids Res 20 (1992) 1717-23, U.S. Pat. No. 5,411,876). Alternatively, the DNA polymerase is affinity immobilized on a solid support prior to the amplification reaction and only released into the reaction mixture by a heat mediated release (Nilsson, J., et al., Biotechniques 22 (1997) 744-51). Both methods, however are time consuming and inconvenient to perform.

Chemical Modification of DNA Polymerase

For this type of hot start PCR, the DNA polymerase is reversibly inactivated as a result of a chemical modification. More precisely, heat labile blocking groups are introduced into the Taq DNA polymerase which renders the enzyme inactive at room temperature (U.S. Pat. No. 5,773,258). These blocking groups are removed at high temperature during a pre-PCR step such that the enzyme is becoming activated. Such a heat labile modification, for example can be obtained by coupling Citraconic Anhydride or Aconitric Anhydride to the Lysine residues of the enzyme (U.S. Pat. No. 5,677,152). Enzymes carrying such modifications are meanwhile commercially available as Amplitaq Gold (Moretti, T., et al., Biotechniques 25 (1998) 716-22) or FastStart DNA polymerase (Roche Molecular Biochemicals). However, the introduction of blocking groups is a chemical reaction which arbitrarily occurs on all sterically available Lysine residues of the enzyme. Therefore, the reproducibility and quality of chemically modified enzyme preparations may vary and can hardly be controlled.

Recombinant Modification of DNA Polymerase

Cold sensitive mutants of Taq Polymerase have been prepared by means of genetic engineering. These mutants differ from the wildtype enzyme in that they lack the N-terminus (U.S. Pat. No. 6,241,557). In contrast to native or wild type recombinant Taq Polymerase, these mutants are completely inactive below 35° C. and thus may be used in some cases for performing a hot start PCR. However, the N-terminal truncated cold sensitive mutant form requires low salt buffer conditions, has a lower processivity as compared to the wild type enzyme and thus can only be used for the amplification of short target nucleic acids. Moreover, since the truncated form lacks 5'-3' exonuclease activity, it can not be used for real time PCR experiments based on the TaqMan detection format.

DNA Polymerase Inhibition by Nucleic Acid Additives

Extension of non-specifically annealed primers has been shown to be inhibited by the addition of short double stranded DNA fragments (Kainz, P., et al., Biotechniques 28 (2000) 278-82). In this case, primer extension is inhibited at temperatures below the melting point of the short double stranded DNA fragment, but independent from the sequence of the competitor DNA itself. However, it is not known, to which extent the excess of competitor DNA influences the yield of the nucleic acid amplification reaction.

Alternatively, oligonucleotide Aptamers with a specific sequence resulting in a defined secondary structure may be used. Such Aptamers have been selected using the SELEX Technology for a very high affinity to the DNA polymerase (U.S. Pat. No. 5,693,502, Lin, Y., and Jayasena, S. D., J Mol Biol 271 (1997) 100-11). The presence of such Aptamers within the amplification mixture prior to the actual thermocycling process itself again results in a high affinity binding to the DNA polymerase and consequently a heat labile inhibition of its activity (U.S. Pat. No. 6,020,130). Due to the selection process, however, all so far available Aptamers can only be used in combination with one particular species of DNA polymerase.

Taq DNA Antibodies

An alternative approach to achieve heat labile inhibition of Taq DNA polymerase is the addition of monoclonal antibodies raised against the purified enzyme (Kellogg, D. E., et al., Biotechniques 16 (1994) 1134-7; Sharkey, D. J., et al., Biotechnology (N Y). 12 (1994) 506-9). Like the oligonucleotide Aptamers, the antibody binds to Taq DNA polymerase with high affinity at ambient temperatures in an inhibitory manner (U.S. Pat. No. 5,338,671). The complex is resolved in a preheating step prior to the thermocycling process itself. This leads to a substantial time consuming prolongation of the amplification as a whole, especially if protocols for rapid thermocycling are applied (WO 97/46706).

U.S. Pat. No. 5,985,619 discloses a specific embodiment for performing PCR using a hot start antibody, wherein besides Taq polymerase, e.g. Exonuclease III from *E. coli* is added as a supplement to the amplification mixture in order to digest unspecific primer dimer intermediates. As disclosed above, Exonuclease III recognizes double-stranded DNA as a substrate, like, for example, target/primer- or target/primer extension product hybrids. Digestion is taking place by means of cleavage of the phosphodiester bond at the 5' end of the 3' terminal deoxynucleotide residue. Since this type of exonuclease is active at ambient temperatures, all unspecifically annealed primers and primer extension products therefore are digested. This results in some embodiments in an even enhanced specificity of the amplification reaction. Yet, digestion of the unspecific primers dependent on the duration of the preincubation time may lead to a substantial and uncontrolled decrease in primer concentration, which in turn may affect the amplification reaction itself.

Usage of Modified Primers Alone or in Combination with Exonucleases

EP 0 799 888 and GB 2293238 disclose an addition of 3' blocked oligonucleotides to PCR reactions. Due to the 3' block, these oligonucleotides can not act as primers. The blocked oligonucleotides are designed to compete/interact with the PCR primers which results in reduction of non-specific products.

Another alternative is the use of phosphorothioate oligonucleotide primers in combination with an exonuclease III in the PCR reaction mixes (EP 0 744 470). In this case, a 3' exonuclease, which usually accepts double stranded as well as single stranded DNA substrates, degrades duplex artifacts such as primer dimers as well as carry over amplicons, while leaving the single stranded amplification primers undegraded. Similarly, the usage of primers with a basic modified 3' ends and template dependent removal by E. coli Endonuclease IV has been suggested (U.S. Pat. No. 5,792,607).

A particular embodiment of the general idea is found in EP 1 275 735. Its specification discloses a composition for performing a nucleic acid amplification reaction comprising (i) a thermostable DNA-Polymerase, (ii) a thermostable 3'-5' Exonuclease, and (iii) at least one primer for nucleic acid amplification with a modified 3' terminal residue which is not elongated by said thermostable DNA-Polymerase as well as methods for performing a PCR reaction using this composition. Furthermore, the method is directed to kits comprising such a composition.

However, it is major drawback of the disclosed alternatives that for each PCR reaction, modified primers are required, which lead to increased requirements regarding increase the cost for each individual assay.

Other PCR Additives

Other organic additives known in the art like DMSO, betaines, and formamides (WO 99/46400; Hengen, P. N., Trends Biochem Sci 22 (1997) 225-6; Chakrabarti, R., and Schutt, C. E., Nucleic Acids Res 29 (2001) 2377-81) result in an improvement of amplification of GC rich sequences, rather than prevention of primer dimer formation. Similarly, heparin may stimulate in vitro run-on transcription presumably by removal of proteins like histones in order to make chromosomal DNA accessible (Hildebrand, C. E., et al., Biochimica et Biophysica Acta 477 (1977) 295-311).

It is also known that addition of single strand binding protein (U.S. Pat. No. 5,449,603) or tRNA, (Sturzenbaum, S. R., Biotechniques 27 (1999) 50-2) results in non-covalent association of these additives to the primers. This association is disrupted when heating during PCR. It was also found that addition of DNA helicases prevent random annealing of primers (Kaboev, O. K., et al., Bioorg Khim 25 (1999) 398-400). Furthermore, poly-glutamate (WO 00/68411) in several cases may be used in order to inhibit polymerase activity at low temperatures.

Moreover, it is known that polyanionic polymerase inhibitors may control the activity of thermostable DNA polymerases dependent on the applied incubation temperature. U.S. Pat. No. 6,667,165 discloses a hot start embodiment, characterized in that inactive polymerase-inhibitor complexes are formed at temperatures below 40° C. Between 40° C. and 55° C., the inhibitor competes with the template DNA for binding to the Taq Polymerase, whereas at temperatures above 55° C., the inhibitor is displaced from the polymerase active site. Yet, the inhibitor tends to reduce the obtainable product yield, when primers with lower annealing temperatures are used.

Magnesium Sequestration

Since thermostable polymerases are known for a long time to be active only in presence of $Mg^{2+}$ cations, a sequestration of magnesium prior to the start of the thermocycling protocol has been attempted in order to avoid mispriming and unspecifying primer extension. As disclosed in U.S. Pat. No. 6,403,341, $Mg^{2+}$ may be present in form of a precipitate and thus unavailable at the beginning of the amplification reaction. Upon temperature increase during the first round of thermocycling, the precipitate dissolves and $Mg^{2+}$ becomes fully available within the first 3 cycles. Such a solution has been shown to be fairly applicable and capable of providing good hot start results. On the other hand, such a solution does not allow the preparation of mastermixes containing all reagents except primer and target nucleic acid which are necessary to perform a nucleic acid amplification reaction. As a consequence, inter-assay data reproducibility and data comparisons are complicated.

In view of the outlined prior art it was an object of the invention to provide an improved alternative composition and method for hot start PCR, which allows for an inhibition of unspecific priming and primer extension not only prior to the amplification process itself but also during the thermocycling process. More precisely, it was an object of the invention to provide an alternative composition and method for hot start PCR, where no extension of unspecifically annealed primers can take place.

SUMMARY OF THE INVENTION

Most thermostable polymerases capable of catalyzing a polymerase chain reaction are dependent on the presence of a divalent cation, usually $Mg^{2+}$. The present invention is based on the principle of generating a hot start effect by adding a divalent cation binding compound to a polymerase chain reaction mixture, which binds divalent cations in a temperature dependent manner.

Thus, in a first aspect, the present invention is directed to a synthetic peptide having a length of not more than 30 amino acids comprising a divalent cation binding site.

Preferably, said synthetic peptide according to the present invention binds said divalent cation with an affinity constant between 0.01 mM and 10 000 μM.

Since most thermostable polymerases are $Mg^{2+}$ dependent, said divalent cation binding site is preferably a motive which binds $Mg^{2+}$.

In a specific embodiment, the synthetic peptide according to the present invention comprises the amino acid sequence motive X1X2X3 at least once, wherein X1 is a negatively charged amino acid, preferentially aspartic acid, X2 is either glycine or an aliphatic amino acid, and X3 is a negatively charged amino acid.

In a second aspect, the present invention is directed to a composition comprising a thermostable DNA polymerase, at least one sort of a divalent cation, preferably $Mg^{2+}$, deoxynucleotides, a buffer, and a synthetic peptide a having a length of not more than 30 amino acids comprising a divalent cation binding site as disclosed above.

Preferably, said composition according to the present invention further comprises at least one nucleic acid compound such as a primer and/or a target nucleic acid that shall become amplified.

In a third aspect, the present invention is directed to a kit comprising a peptide as disclosed above, and a thermostable DNA polymerase.

In a fourth aspect the present invention is directed to a method for amplification of a specific target nucleic acid comprising the steps of providing a sample suspected to contain said target nucleic acid, adding a composition as disclosed above, and performing a polymerase chain reaction.

In a specific embodiment, said polymerase chain reaction is monitored in real time.

In a further specific embodiment, the amplification product generated by said amplification is subjected to a melting curve analysis.

BRIEF DESCRIPTION OF DRAWINGS

FIG. 1 shows the effect of magnesium binding peptide with the sequence DIETDIET (SEQ ID NO: 9) as disclosed in Example 1. The primer dimer product formation (⇒) is suppressed when the peptide is present in the PCR reaction mixture without influence on specific product formation (→).

Lanes 1: Molecular Weight Marker VI from Roche Applied Science
2, 7: 50 ng of template DNA
3, 8; 25 ng of template DNA
4, 9: 10 ng of template DNA
5, 10: 5 ng of template DNA
6, 11: 1 ng of template DNA Products of lanes 2 to 6 were amplified in the absence of peptide, products of lanes 7 to 11 in the presence of 2 mM of the peptide with the sequence H-DIETDIET-NH2 (SEQ ID NO: 9).

The primer dimer product formation (⇒) is suppressed when the peptide is present in the PCR reaction mixture without influence on specific product formation (→).

FIG. 2

Figure 2:
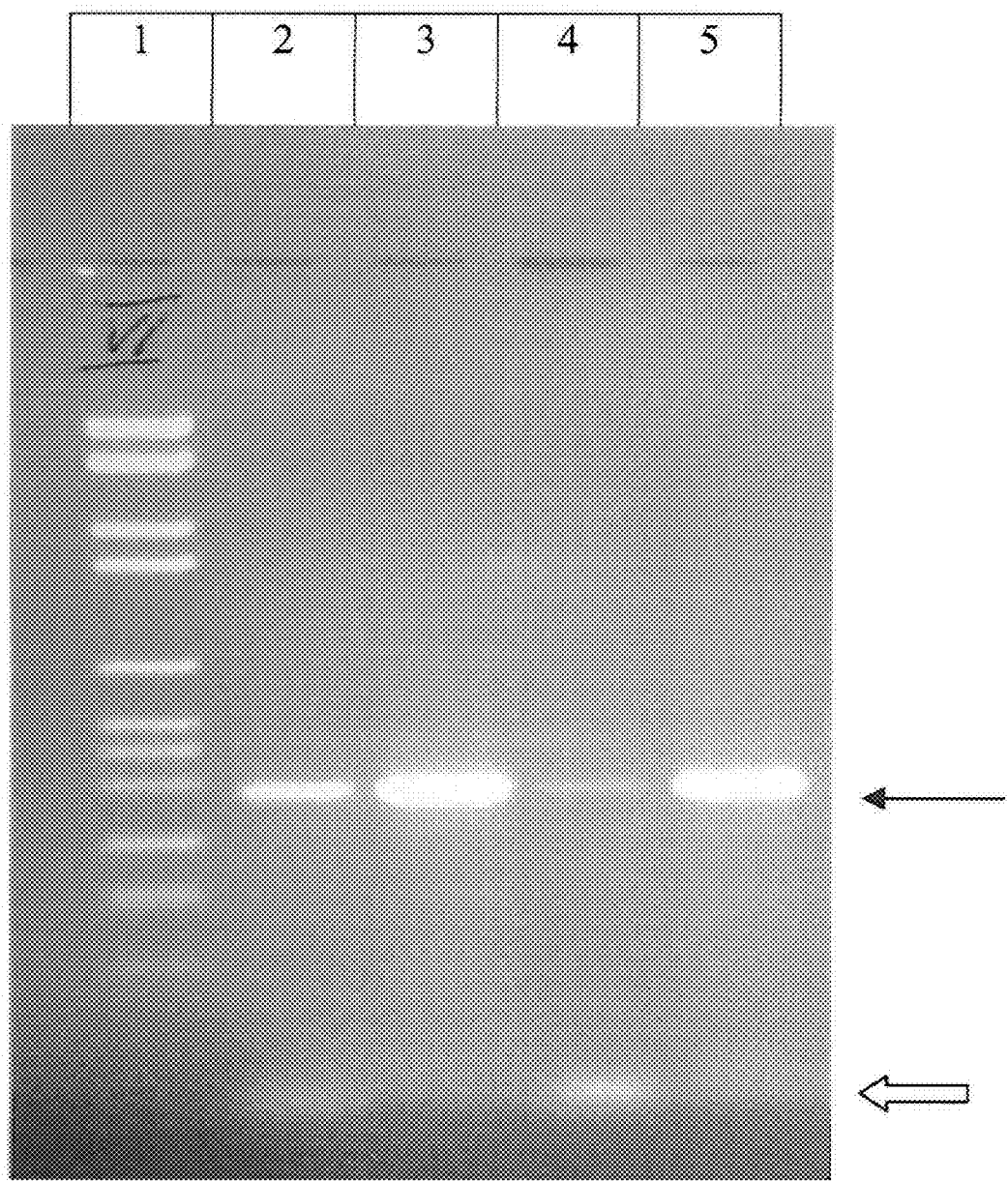

FIG. 2 shows the effect of magnesium binding peptide of the sequence H-FDGDFDGD-NH2 (SEQ ID NO: 10). Primer dimer product, formation (⇒) is reduced when the peptide is present in the PCR reaction, in parallel an increase of the specific product formation (→) is observed.

Lane 1: Molecular Weight Marker VI from Roche Applied Science
2: 25 ng of target DNA, no peptide
3: 25 ng of target DNA, 3 mM of peptide
4: 10 ng of target DNA, no peptide
5: 10 ng of target DNA, 3 mM of peptide

FIG. 3

Figure 3A:
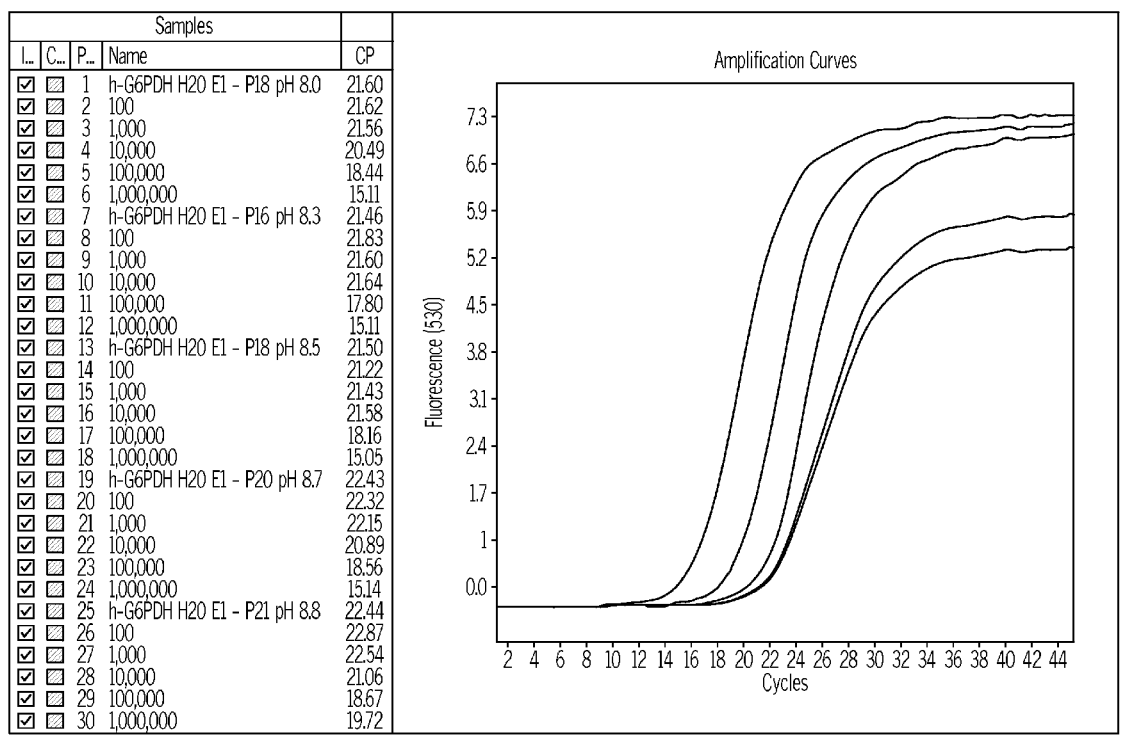

FIG. 3a: RT-PCR with 102 to 106 copies of G6PDH RNA in the absence of magnesium binding peptide.

Figure 3B:
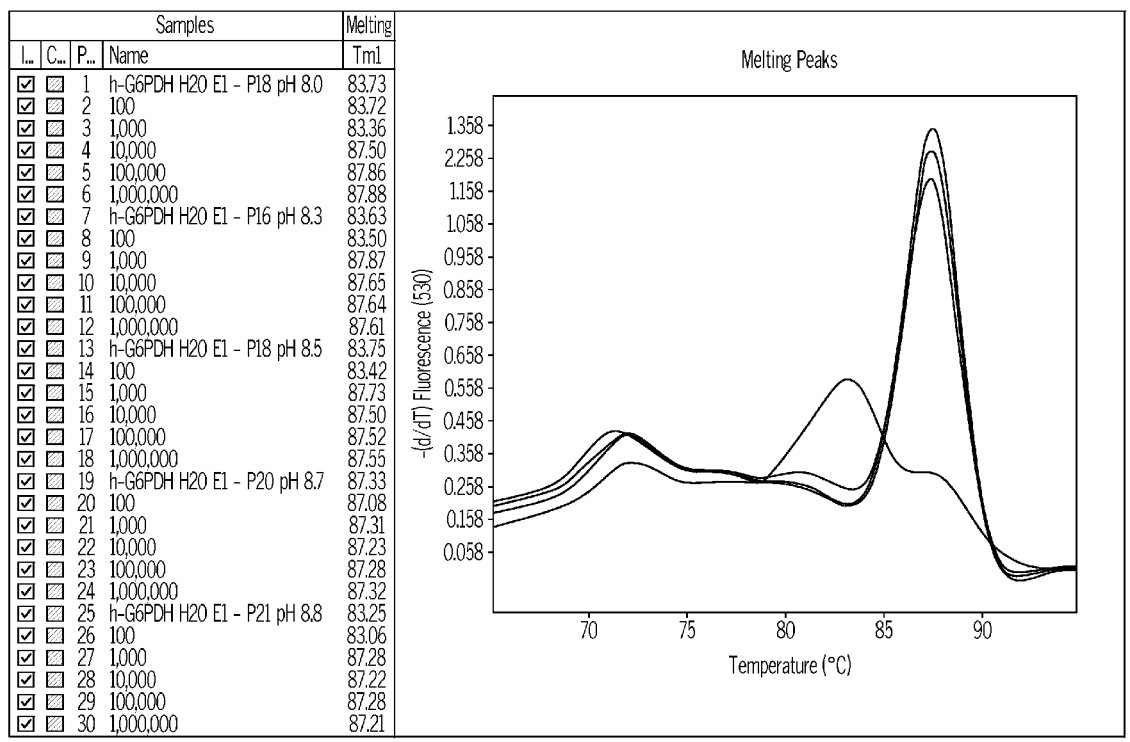

FIG. 3b: Melting curve analysis of RT-PCR with 102 to 106 copies of G6PDH RNA in the absence of magnesium binding peptide.

Figure 3C:
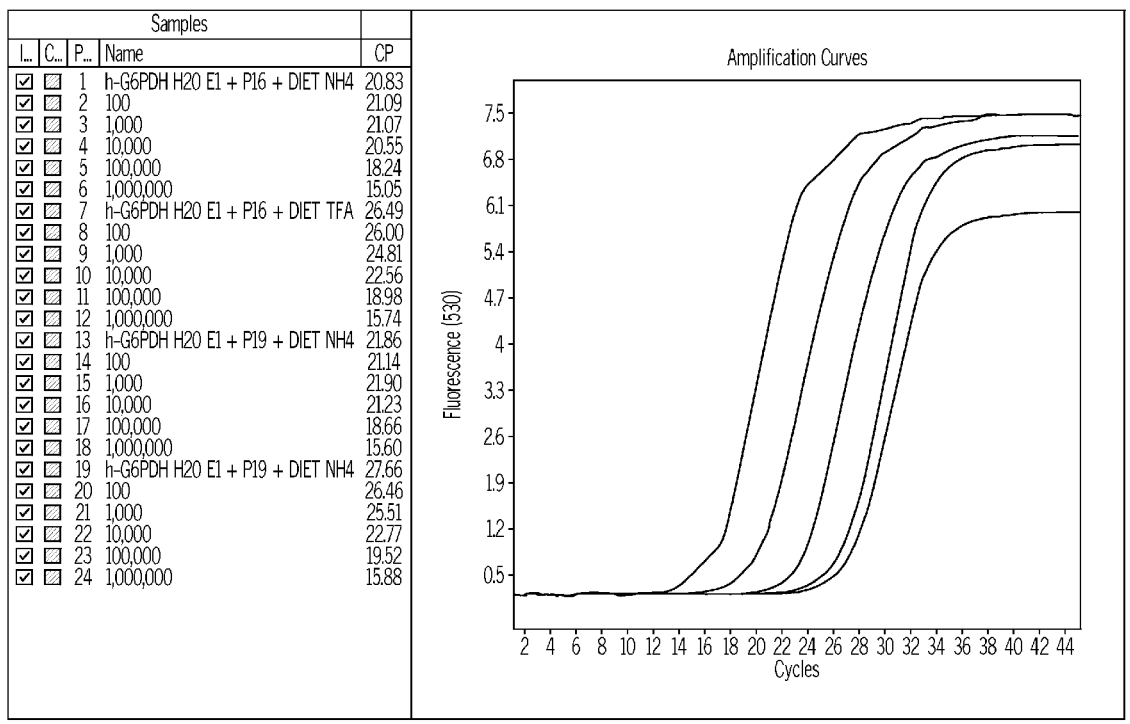

FIG. 3c: RT-PCR with 102 to 106 copies of G6PDH RNA in the presence of 1 mM of magnesium binding peptide.

Figure 3D:
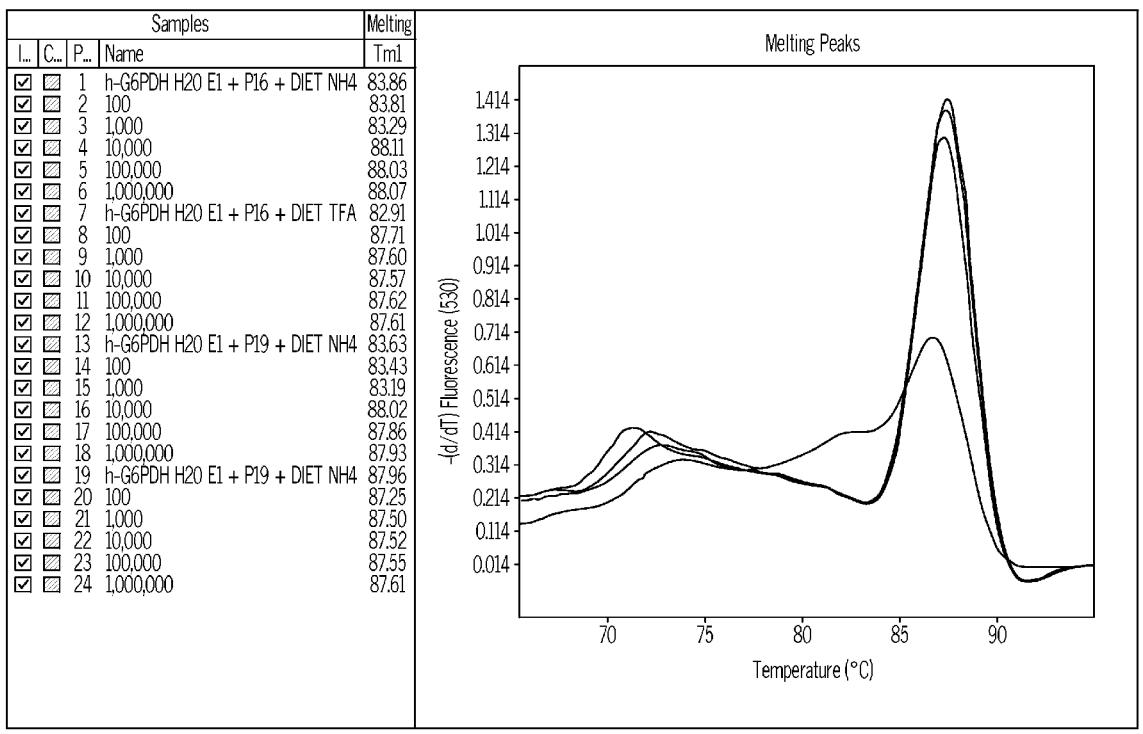

FIG. 3d: Melting curve analysis of RT-PCR with 102 to 106 copies of G6PDH RNA in the presence of 1 mM of magnesium binding peptide.

FIG. 4

Products of lanes 2 to 6 were amplified in the absence of the peptide H-DIETDIETDIET-NH2 (SEQ ID NO: 8), products of lanes 7 to 11 in the presence of 2.0 mM of the peptide with the sequence H-DIETDIETDIET-NH2 (SEQ ID NO: 8). The primer dimer product formation (⇒) is suppressed when the peptide is present in the PCR reaction mixture without influence on specific product formation (→).

Lanes 1, 12: Molecular Weight Marker V from Roche Applied Science
2, 7: 50 ng of template DNA
3, 8: 25 ng of template DNA
4, 9: 10 ng of template DNA
5, 10: 5 ng of template DNA
6, 11: 1 ng of template DNA

DETAILED DESCRIPTION OF THE INVENTION

Most thermostable polymerases capable of catalyzing a polymerase chain reaction are dependent on the presence of a divalent cation, usually $Mg^{2+}$. The present invention is based on the principle of generating a hot start effect by adding a divalent cation binding compound to a polymerase chain reaction mixture, which binds divalent cations in a temperature dependent manner.

Thus, in a first aspect, the present resent invention is directed to a synthetic peptide having a length of not more than 30 amino acids comprising a divalent cation binding site. Smaller synthetic peptides having a length of less than 17 amino acids may also be used. Since a binding site for divalent cations requires at least 3-4 amino acid residues (see below), the lower size limit is a peptide consisting of 3-4 amino acids representing a monomer of a divalent cation binding site. It is also within the scope of the present invention, if said synthetic peptides contain more than one divalent cation binding site motives, i.e. if they contain said motives twice, three times or four times. However, said synthetic peptides according to the present invention in addition to amino acids representing a divalent cation binding sequence motive may contain further amino acids, which are not part of such a motive, but may contribute to other features of said peptide. For example, additional amino acid residues may increase the solubility of said peptides in different solvents.

In the context of the present invention, the term "synthetic peptide" is defined as a chain of amino acids connected by amide bonds, which has been chemically synthesized by means of condensation. Explicitly excluded, however, are peptides or peptide fragments which have been obtained from living organisms by means of isolation and (optional) fragmentation.

Such synthetic peptides can be used according to methods which are generally well known in the art. The synthesis is based on an automated cycling reaction wherein amino acids are connected to the nascent peptide chain in a condensation reaction by means of forming an amide bond. Reactive side chains of the coupled amino acids are covered by appropriately removable protective groups. A comprehensive overview of the state of the art is given in Fields, G. B., Noble, J. Peptide Protein Res. 35 (1990) 161-214. Such a chemical synthesis results in the generation of peptides having a typical $H_2N$-Terminus (usually referenced as "H") and a C-Terminus with a carboxy-amidate (usually referenced as "—$NH_2$").

The peptides according to the present invention are capable of binding divalent cations. The strength of binding predominantly depends on the nature of the divalent cation in conjunction with the primary peptide sequence motive of the peptide. Preferably, said synthetic peptide according to the present invention binds said divalent cation with an affinity constant between 0.01 mM and 10 000 μM at neutral pH. Compounds with stronger affinity rates such as EDTA have been shown to result in detrimental effects when added to an amplification reaction, whereas on the other hand, a minimal affinity rate is required in order to generate a measurable positive effect when such a peptide compound is added to a nucleic acid amplification reaction. More preferably, said affinity constant has a value between 0.1 mM and 1000 mM. Most preferably, said affinity constant has a value between 1 mM and 100 mM.

Since most thermostable polymerases are $Mg^{2+}$ dependent, said divalent cation binding site is preferably a motive which binds $Mg^{2+}$.

In the section below, the following classification of amino acids is applied.
No Subclass:
  Glycine (Gly) G
  Proline (Pro) P
Non Polar, Aliphatic:
  Alanine (Ala), A
  Valine (Val), V
  Leucine (Leu), L
  Isoleucine (Ile) I
Aromatic:
  Phenylalanine (Phe), F
  Tyrosine (Tyr), Y
  Tryptophane (Trp) W
Polar, Uncharged:
  Serine (Ser), S
  Threonine (Thr), T
  Cysteine (Cys), C
  Methionine (Met), M
  Asparagine (Asn), N
  Glutamine (Gln), Q
Positively Charged:
  Lysine (Lys), K
  Arginine (Arg), R
  Histidine (His) H
Negatively Charged:
  Aspartic acid (Asp), D
  Glutamic acid (Glu) E Preferably, the synthetic peptide according to the present invention comprises the amino acid sequence motive X1X2X3 at least once, wherein X1 is a negatively charged amino acid, preferentially aspartic acid, X2 is either glycine or an aliphatic amino acid, and X3 is a negatively charged amino acid.

In one embodiment, X3 is a Glutamic acid. If this is the case, X2 is preferably Isoleucine. Also preferably, c-terminal adjacent to X3 there is an X4 which is a polar, uncharged amino acid such as Threonine.

Most preferably, X2 is Isoleucine and c-terminal adjacent to X3 there is an X4 which is a polar uncharged amino acid such as Threonine.

In another embodiment, X3 is an Aspartic acid. If this is the case, X2 is preferably Glycine. Also preferably, N-terminal adjacent to X1 there is an X0 which is an aromatic amino acid such as Phenylalanine.

Most preferably, X2 is Isoleucine and N-terminal adjacent to X1 there is an X0 which is an aromatic amino acid such as Phenylalanine.

In a second aspect, the present invention is directed to a composition comprising a thermostable DNA polymerase, at least one sort of a divalent cation, preferably $Mg^{2+}$, deoxynucleotides, a buffer, and a synthetic peptide having a length of not more than 30 amino acids comprising a divalent cation binding site as disclosed above.

Such a composition according to the present invention is being used to perform a nucleic acid amplification reaction in the form of a polymerase chain reaction (PCR).

As thermostable polymerases, a great variety of enzymes may be used. Preferably, said thermostable DNA polymerase is selected from a group consisting of *Aeropyrum pernix, Archaeoglobus fulgidus, Desulfurococcus* sp. Tok., *Methanobacterium thermoautotrophicum, Methanococcus* sp. (e.g. jannaschii, voltae), *Methanothermus fervidus, Pyrococcus* species (furiosus, species GB-D, woesii, abysii, horikoshii, KOD, Deep Vent, Proofstart), *Pyrodictium abyssii, Pyrodictium occultum, Sulfolobus* sp. (e.g. acidocaldarius, solfataricus), *Thermococcus* species (zilligii, barossii, fumicolans, gorgonarius, JDF-3, kodakaraensis KODI, litoralis, species 9 degrees North-7, species JDF-3, gorgonarius, TY), *Thermoplasma acidophilum, Thermosipho africanus, Thermotoga* sp. (e.g., maritima, neapolitana), *Methanobacterium thermoautotrophicum, Thermus* species (e.g. aquaticus, brockianus, filiformis, flavus, lacteus, rubens, ruber, thermophilus, ZO5 or Dynazyme). Also within the scope of the present invention are mutants, variants or derivatives thereof, chimeric or "fusion-polymerases" e.g. Phusion (Finnzymes or New England biolabs, Catalog No. F-530S) or iProof (Biorad, Cat. No. 172-5300), Pfx Ultima (Invitrogen, Cat. No. 12355012) or Herculase II Fusion (Stratagene, Cat. No. 600675). Furthermore, compositions according to the present invention may comprise blends of one or more of the polymerases mentioned above.

In one embodiment, the thermostable DNA Polymerase is a DNA dependent polymerase. In another embodiment, the thermostable DNA polymerase has additional reverse transcriptase activity and may be used for RT-PCR. One example for such enzyme is *Thermus thermophilus* (Roche Diagnostics cat. No: 11 480 014 001). Also within the scope of the present invention are blends of one or more of the polymerases compiled above with retroviral reverse transcriptases, e.g. polymerases from MMLV, AMV, AMLV, HIV, EIAV, RSV and mutants of these reverse transcriptases.

The synthetic peptide having a length of not more than 30 amino acids comprising a divalent cation binding site is present in a concentration which allows for a "hot start effect", once the composition is used to amplify a target nucleic acid. Usually, the peptide comprising the $Mg^{2+}$ binding site may be present in a final concentration between 0.1 and 10 mM. Preferably, the peptide comprising the $Mg^{2+}$ binding site is present between 0.5 and 5 mM. Highly preferred are concentrations between 1 and 3 mM.

The concentrations of the DNA polymerase, the deoxynucleotide and the other buffer components are present in standard amounts, the concentrations of which are well known in the art. The $Mg^{2+}$ concentration may vary between 0.1 mM and 3 mM and is preferably adapted and experimentally optimized. However, since the concentration optimum usually depends on the actual primer sequences used, it can not be predicted theoretically.

In addition to the compositions disclosed above it is also within the scope of the present invention, if these compositions further comprise at least one nucleic acid compound. For example, such a composition may comprise at least one pair of amplification primers useful for performing a nucleic acid amplification reaction. A composition according to the present invention may also be a PCR reaction mixture, which additionally comprises an at least partially purified nucleic acid sample, from which a target nucleic acid sequence suspected to be present in said sample shall be amplified.

Furthermore, such a composition may comprise fluorescent compounds for detecting a respective amplification product in real time and respectively 2, 3, 4, or 5-6 differently labeled hybridization probes not limited to but being selected from a group consisting of FRET hybridization probes, TaqMan probes, Molecular Beacons and Single labeled probes, useful for methods of detection as they will be disclosed below. Alternatively, such a composition may contain a dsDNA binding fluorescent entity such as SYBR Green (Molecular Probes Inc.) which emits fluorescence only when bound to double stranded DNA.

In a third aspect, the present invention is directed to a kit at least comprising a thermostable DNA Polymerase and a synthetic $Mg^{2+}$ binding peptide as disclosed above, and preferably, such a kit comprises at least a thermostable DNA Polymerase, a synthetic $Mg^{2+}$ binding peptide as disclosed above, and a $MgCl_2$ stock solution in order to adjust the final $Mg^{2+}$ concentration. Most preferably, such a kit comprises at least a thermostable DNA Polymerase, a synthetic $Mg^{2+}$ binding peptide as disclosed above, a $MgCl_2$ stock solution in order to adjust the final $Mg^{2+}$ concentration, a mixture of deoxynucleoside-tri-phosphates, and a buffer.

In addition, such a kit according to the present invention may be a parameter specific kit comprising at least one pair of amplification primers. Such a kit may also comprise multiple pairs of amplification primers and preferably 2, 3, 4 or 5-pairs of amplification primers.

Furthermore, such a kit may comprise fluorescent compounds for detecting a respective amplification product in real time and respectively 2, 3, 4, or 5-6 differently labeled hybridization probes not limited to but being selected from a group consisting of FRET hybridization probes, TaqMan probes, Molecular Beacons and Single labeled probes, useful for methods of detection as they will be disclosed below. Alternatively, such a kit may contain a dsDNA binding fluorescent entity which emits fluorescence only when bound to double stranded DNA. For example, such a kit may comprise SYBR Green.

In one exemplary embodiment, such a kit is specifically adapted to perform one-step RT-PCR and comprises a blend of Taq DNA Polymerase and a reverse transcriptase such as AMV reverse transcriptase. In a further exemplary particular embodiment, such a kit is specifically adapted to perform one-step real time RT-PCR and comprises a nucleic acid detecting entity such as SYBR Green or a fluorescently labeled nucleic acid detection probe.

The different components may be stored each individually in different vessels. Alternatively, the different components may be stored all together in one storage vessel. Also alternatively, arbitrarily selected combinations of only a subset of the components may be stored together. In a preferred embodiment, components like the polymerase enzyme or the enzyme plus reaction buffer containing $MgU_2$, dNTPs and the peptide are stored together.

In a fourth aspect the present invention is directed to a method for amplification of a specific target nucleic acid comprising the steps of providing a sample suspected to contain said target nucleic acid, adding a composition as disclosed above, and performing a nucleic acid amplification reaction.

Methods for performing and optimizing nucleic acid amplification reactions are well known in the art. In particular, the most common method used in the art is the polymerase chain reaction as disclosed in detail in U.S. Pat. Nos. 4,683,195, 4,683,202 and 4,965,188.

In particular, the method according to the present invention comprises the steps of providing a sample suspected to contain a target nucleic acid that shall be amplified, providing a synthetic peptide having a length of not more than 30 amino acids comprising a divalent cation binding site, providing DNA polymerase, dNTPs, a buffer and a $Mg^{2+}$ salt, and providing a pair of amplification primers designed to specifically amplify a predefined target nucleic acid.

Addition of all components mentioned can be done in arbitrary order. However, in order to achieve a hot start effect, i.e. in order to prevent a mispriming and subsequent primer extension at lower temperatures prior to the thermocycling amplification protocol itself, it is important that said synthetic peptide is being added to the reaction mixture, before the DNA polymerase, the dNTPs and the amplification primers are combined.

Although the mechanism how said synthetic peptides comprising a divalent cation binding site result in more specific amplification reactions is not known in detail, it is reasonable to assume that at lower temperatures, the peptide forms a complex with $Mg^{2+}$ which itself is known to be a co-factor of DNA polymerases in primer extension reactions. Quantitative complex formation results in a decrease in the concentration of free $Mg^{2+}$ with the consequence that the DNA Polymerase activity is inactivated due to a lack of availability of its cofactor. After initiation of the temperature cycling protocol, the thermo-labile complex between the synthetic peptide and the divalent cation is resolved, and $Mg^{2+}$ is available again as a cofactor for Polymerase catalyzed primer extension reactions.

Preferably, the synthetic peptide added during nucleic acid amplification comprises the amino acid sequence motive X1X2X3 at least once, wherein X1 is a negatively charged amino acid, preferentially Aspartic acid, X2 is either Glycine or an aliphatic amino acid, and X3 is a negatively charged amino acid.

In one embodiment, X3 is a Glutamic acid. If this is the case, X2 is preferably Isoleucine. Also preferably, C-terminal adjacent to X3 there is an X4 which is a polar, uncharged amino acid such as Threonine.

Most preferably, X2 is Isoleucine and C-terminal adjacent to X3 there is an X4 which is a polar uncharged amino acid such as Threonine.

In another embodiment, X3 is Aspartic acid. If this is the case, X2 is preferably Glycine. Also preferably, N-terminal adjacent to X1 there is an X0 which is an aromatic amino acid such as Phenylalanine.

Most preferably, X2 is Isoleucine and N-terminal adjacent or X1 there is an X0 which is an aromatic amino acid such as Phenylalanine.

In a specific embodiment, said Polymerase Chain Reaction is monitored in real time. There are different detection formats for such a monitoring.

TaqMan Format

A single-stranded Hybridization Probe is labeled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the Tag Polymerase during the subsequent elongation phase. As a result the excited fluorescent component and the quencher are spatially separated from one another and thus a fluorescence emission of the first component can be measured. TaqMan probe assays are disclosed in detail in U.S. Pat. Nos. 5,210,015, 5,538,848, and 5,487,972. TaqMan hybridization probes and reagent mixtures are disclosed in U.S. Pat. No. 5,804,375.

Releasing Formats

Moreover, two other formats restricted to allele specific detection have been disclosed recently which are based on the principle of specific detection of a release of a labeled 3' terminal nucleotide due to a match or mismatch situation regarding its binding to the target nucleic acid. U.S. Pat. No. 6,391,551 discloses a method, characterized in that the 3' terminal nucleotide of a hybridization probe is released by a depolymerizing enzyme in case a perfect match between target sequence and probe has occurred. Similarly, EP 0 930 370 suggests to use a primer labeled with a reporter and a quencher moiety, characterized in that a 3'-5' proofreading activity removes one moiety in case no perfect match between primer and amplification target has occurred.

Molecular Beacons

These hybridization probes are also labeled with a first component and with a quencher, the labels preferably being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118,801).

FRET Hybridization Probes

The FRET Hybridization Probe test format is especially useful for all kinds of homogenous hybridization assays (Matthews, J. A., and Kricka, L. J., Analytical Biochemistry 169 (1988) 1-25). It is characterized by two single-stranded hybridization probes which are used simultaneously and are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected. Alternatively to monitoring the increase in fluorescence of the FRET acceptor component, it is also possible to monitor fluorescence decrease of the FRET donor component as a quantitative measurement of hybridization event.

In particular, the FRET Hybridization Probe format may be used in real time PCR, in order to detect the amplified target DNA. Among all detection formats known in the art of real time PCR, the FRET-Hybridization Probe format has been proven to be highly sensitive, exact and reliable (WO 97/46707; WO 97/46712; WO 97/46714). As an alternative to the usage of two FRET hybridization probes, it is also possible to use a fluorescent-labeled primer and only one labeled oligonucleotide probe (Bernard, P. S., et al., Analytical Biochemistry 255 (1998) 101-107). In this regard, it may be chosen arbitrarily, whether the primer is labeled with the FRET donor or the FRET acceptor compound.

Single Label Probe (SLP) Format

This detection format consists of a single oligonucleotide labeled with a single fluorescent dye at either the 5'- or 3'-end (WO 02/14555). Two different designs can be used for oligo labeling: G-Quenching Probes and Nitroindole-Dequenching probes. In the G-Quenching embodiment, the fluorescent dye is attached to a C at oligo 5'- or 3'-end. Fluorescence decreases significantly when the probe is hybridized to the target, in case two G's are located on the target strand opposite to C and in position 1 aside of complementary oligonucleotide probe. In the Nitroindole Dequenching embodiment, the fluorescent dye is attached to Nitroindole at the 5'- or 3'-end of the oligonucleotide. Nitroindole somehow decreases the fluorescent signaling of the free probe. Fluorescence increases when the probe is hybridized to the target DNA due to a dequenching effect.

SYBR Green Format

It is also within the scope of the invention, if real time PCR is performed in the presence of an additive according to the invention in case the amplification product is detected using a double stranded nucleic acid binding moiety. For example, the respective amplification product can also be detected according to the invention by a fluorescent DNA binding dye which emits a corresponding fluorescence signal upon interaction with the double-stranded nucleic acid after excitation with light of a suitable wavelength. The dyes SYBR GreenI and SybrGold (Molecular Probes) have proven to be particularly suitable for this application. Intercalating dyes can alternatively be used. However, for this format, in order to discriminate the different amplification products, it is necessary to perform a respective melting curve analysis (U.S. Pat. No. 6,174,670).

A further aspect of the present invention is directed to methods characterized in that a synthetic peptide having a length of not more than 30 amino acids comprising a divalent cation binding site as disclosed above is used for real time PCR and subsequent melting curve analysis.

Due to the fact that real time amplicon detection with SYBR Green format can not discriminate between specific products and amplification artifacts such as primer/dimers, a subsequent melting curve analysis is usually performed. After completion of the PCR-reaction, the temperature of the sample is constitutively increased, and fluorescence is detected as long as SYBR Green is bound to the double stranded DNA present in the samples. Upon dissociation of the double stranded DNA the signal decreases immediately. This decrease is monitored with an appropriate fluorescence versus temperature-time plot such that a first derivative value can be determined, at which the maximum of fluorescence decrease is observed. Since primer/dimer double stranded DNAs are usually short, dissociation into single stranded DNA occurs at lower temperatures as compared to the dissociation of the double stranded specific amplification product.

If during such a melting curve analysis, a synthetic peptide with a divalent cation binding site is present within the sample, much sharper curves are obtained in many cases, when the first derivative of a respective fluorescence versus temperature-time plot is determined.

Besides PCR and real time PCR, FRET hybridization probes are used for melting curve analysis. In such an assay, the target nucleic acid is amplified first in a typical PCR reaction with suitable amplification primers. The hybridization probes may already be present during the amplification reaction or added subsequently. After completion of the PCR-reaction, the temperature of the sample is constitutively increased, and fluorescence is detected as long as the hybridization probe was bound to the target DNA. At melting temperature, the hybridization probes are released from their target, and the fluorescent signal is decreasing immediately down to the background level. This decrease is monitored with an appropriate fluorescence versus temperature-time plot such that a first derivative value can be determined, at which the maximum of fluorescence decrease is observed.

If during such a melting curve analysis, Synthetic peptide having a length of not more than 30 amino acids comprising a divalent cation binding site is present within the sample, much sharper curves are obtained, when the first derivative of a respective fluorescence versus temperature-time plot is determined. Similar effects can be observed, if either molecular beacons or single labeled probes are used as detecting entities for melting curve analysis.

The following examples, sequence listing and figures are provided to aid the understanding of the present invention, the true scope of which is set forth in the appended claims. It is understood that modifications can be made in the procedures set forth without departing from the spirit of the invention.

EXAMPLES

Example 1

A peptide with the sequence H-DIETDIET-NH2 (SEQ ID NO: 9) was synthesized, HPLC purified, lyophilized and dissolved in 30 mM Tris-HCl, pH 8.5. PCR reactions were performed in 50 µl volume containing 50 ng, 25 ng, 10 ng, 5 ng or 1 ng of human genomic DNA, 2.5 units Taq polymerase (Roche Applied Science Cat. No. 11146165001), 0.4 mM forward primer (aga cag tac agc cag cct ca) (SEQ ID No: 1), 0.4 mM reverse primer (gac ttc aaa ttt ctg etc ctc) (SEQ ID NO: 2), 0.2 mM dATP, dCTP, dGTP and dCTP, Taq PCR reaction buffer (Roche Applied Science Cat. No. 11146165001), with and without H-DIETDIET-NH2-peptide (SEQ ID NO: 9). The PCR was performed as follows: 2 min at 94° C., 35 cycles with 10 sec at 94° C., 30 sec at 60° C. and 30 sec at 72° C. and a final elongation step over 7 mM at 72° C. The PCR products were analyzed by agarose gel electrophoresis.

Figure 1:
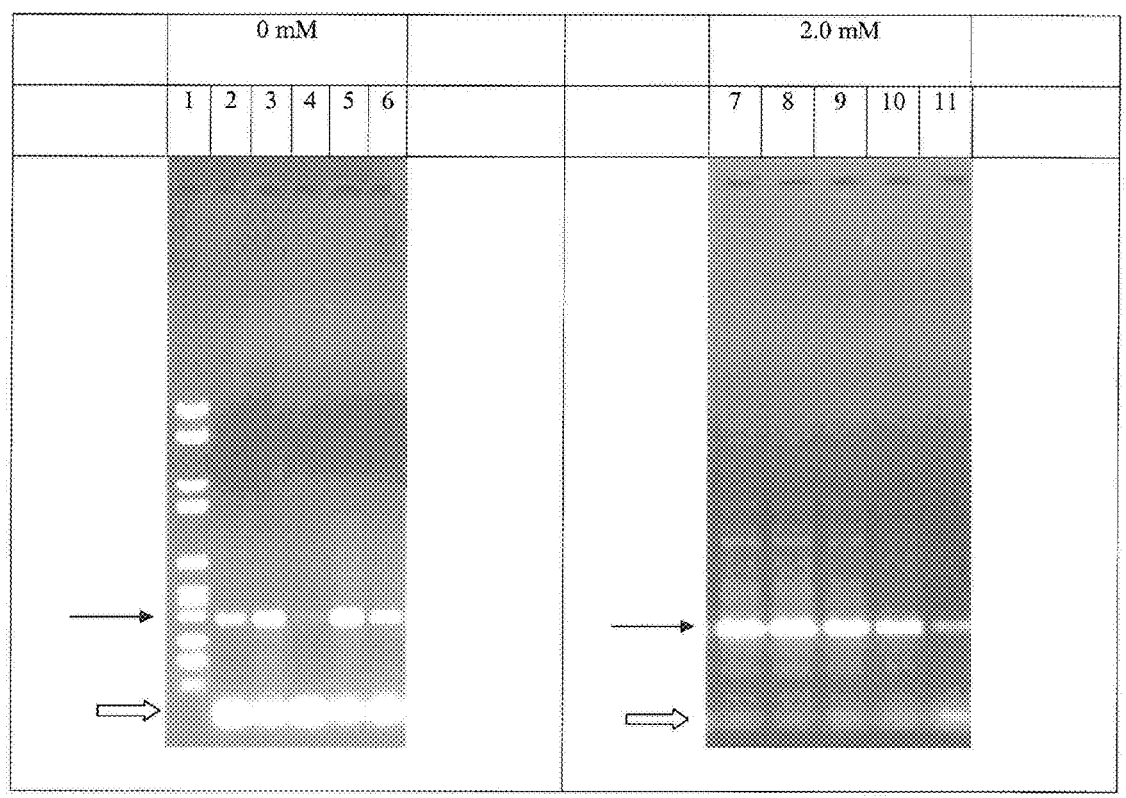
FIG. 1

As it can be seen in FIG. 1, addition of 2.0 mM of the disclosed peptide results in a significant decrease of generation of primer/dimer amplification products.

Example 2

Analysis of a peptide with the sequence H-FDGDFDGD-NH2 (SEQ ID NO: 10). PCR reactions were performed in 50 µl volume containing 25 ng or, 10 ng of human genomic DNA, 2.5 units Taq polymerase (Roche Applied Science Cat. No. 11146165001), 0.4 mM forward primer (aga cag tac age cag cct ca) (SEQ ID NO: 1), 0.4 mM reverse primer (agt atg ccc ccg cac agg a) (SEQ ID NO: 3), 0.2 mM dATP, dCTP, dGTP and dCTP, Taq PCR reaction buffer (Roche Applied Science Cat. No. 11146165001), with and without H—FDGDFDGD —NH2-peptide (SEQ ID NO: 10). The PCR cycling conditions were as follows: 2 min at 94° C., 35 cycles with 10 sec at 94° C., 30 sec at 60° C. and 30 sec at 72° C. and a final elongation step over 7 mM at 72° C. The PCR products were analyzed by agarose gel electrophoresis.

As it can be seen in FIG. 2, addition of 3 mM H-FDGD-FDGD-NH2 (SEQ ID NO: 10) results in decreased primer/dimer product formation. In parallel an increase of the specific product formation is observed.

Example 3

The peptide with the sequence H-DIETDIET-NH2 (SEQ ID NO: 9) was analyzed in real time RT-PCR. PCR reactions were performed in 20 µl volume containing $10^2$, $10^3$, $10^4$, $10^5$ and $10^6$ copies of RNA standard available in the LIGHTCYCLER (Roche Diagnostics GmbH) h-G6PDH Housekeeping gene kit from Roche Applied Science (Cat. No.: 3261883), 2.4 units Transcriptor and 1.6 units FastStart polymerase, reaction buffer from the LIGHTCYCLER RNA Amplification Kit SYBR Green (Roche Applied Science Cat. No. 12 015 137 001), 0.5 mM forward primer (ggg tgc atc ggg tga cct g) (SEQ ID NO: 4), 0.5 mM reverse primer (age cac tgt gag gcg gga) (SEQ ID NO: 5), with and without 1 mM H-DIET-DIET-NH2-peptide (SEQ ID NO: 9). The PCR was performed in a LIGHTCYCLER 2.0 as follows: 10 min at 55° C., 10 min at 95° C., 45 cycles with 10 sec at 95° C., 10 sec at 55° C. and 13 sec at 72° C.

The result of this example is shown in FIG. 3. It illustrates that a magnesium binding peptide reduces primer-dimer formation in RT-PCR. The amplification curves (FIG. 3a) show that in the absence of peptide unspecific product is formed. PCR products amplified from 102, 103, and 104 copies of target are detected at similar cp-values. The amplification curves may be derived from several products formed. In the melting curve analysis depicted in FIG. 3b two melting profiles are detectable with 103 and 102 copies of target RNA. With these dilutions of target the melting curves show two products.

FIG. 3c shows amplification curves in the presence of 1 mM magnesium binding peptide. The amplification products of the target dilutions are detected at increasing crossing points, the amplification curves are well separated. An increase of specificity compared to the experiment without magnesium binding peptide is also observed in the melting curve analysis of FIG. 3d. One melting curve with the Tm of the specific product is exclusively detected the target dilutions from 106 to 103. In the sample with 102 copies of target the main product is the specific product, very little primer-dimer is observed.

Example 4

Figure 4:
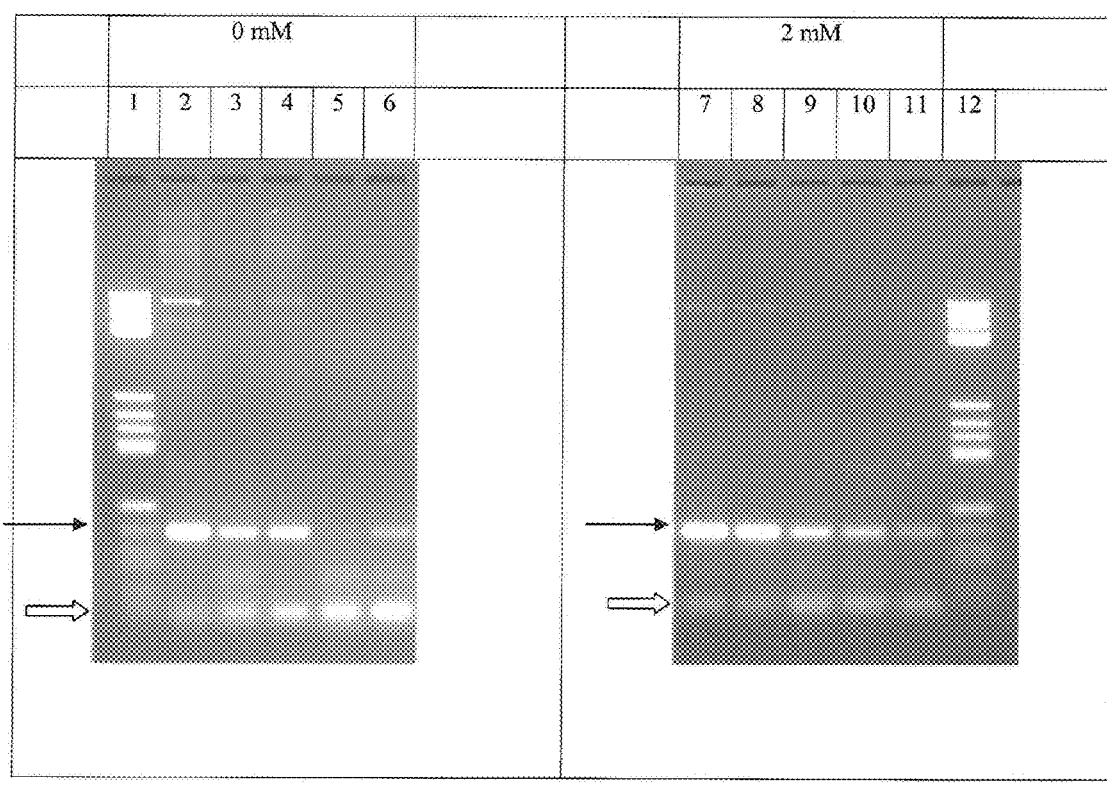

A peptide with the sequence H-DIETDIETDIET-NH2 (SEQ ID NO: 8) was synthesized, HPLC purified, lyophilized and dissolved in 30 mM Tris-HCl, pH 8.5. PCR reactions were performed in 50 µl volume containing 50 ng, 25 ng, 10 ng, 5 ng or 1 ng of human genomic DNA, 2.5 units Taq polymerase (Roche Applied Science Cat. No. 11146165001), 0.4 mM forward primer (cac ccc gtg ctg ctg acc ga) (SEQ ID NO: 6), 0.4 mM reverse primer (agg gag gcg gee acc aga ag) (SEQ ID NO: 7), 0.2 mM dATP, dCTP, dGTP and dCTP, Taq PCR reaction buffer (Roche Applied Science Cat. No. 11146165001), with and without H-DIETDIETDIET-NH2 (SEQ ID NO: 9) peptide in amounts as indicated in FIG. 4. The PCR was performed as follows: 2 min at 94° C., 35 cycles with 10 sec at 94° C., 30 sec at 65° C. and 15 sec at 72° C. and a final elongation step over 7 min at 72° C. The PCR products were analyzed by agarose gel electrophoresis.

FIG. 4 shows the effect of magnesium binding peptide with the sequence DIETDIETDIET (SEQ ID NO: 8). The primer dimer product formation (⇒) is suppressed when the peptide is present in the PCR reaction mixture without influence on specific product formation (→).

Example 5

A peptide with the sequence H-DIET-NH2 (SEQ ID NO: 11) was synthesized, HPLC purified, lyophilized and dissolved in 30 mM Tris-HCl, pH 8.5. PCR reactions were performed in 50 µl volume containing 50 ng, 25 ng, 10 ng, 5 ng or 1 ng of human genomic DNA, 2.5 units Taq polymerase (Roche Applied Science Cat. No. 11146165001), 0.4 mM forward primer (aga cag tac agc cag cct ca) (SEQ ID NO: 1), 0.4 mM reverse primer (gac ttc aaa ttt ctg etc ctc) (SEQ ID NO: 2), 0.2 mM dATP, dCTP, dGTP and dCTP, Taq PCR reaction buffer (Roche Applied Science Cat. No. 11146165001), with and without H-DIET-NH2-peptide (SEQ ID NO: 11). The PCR was performed as follows: 2 min at 94° C., 35 cycles with 10 sec at 94° C., 30 sec at 60° C. and 30 sec at 72° C. and a final elongation step over 7 min at 72° C. The PCR products were analyzed by agarose gel electrophoresis. A decrease in primer/dimer formation was observed in the presence of at least 3 mM H-DIET-NH2 (SEQ ID NO: 11).

What is claimed is:

1. A synthetic peptide consisting of a divalent cation binding site selected from the group consisting of H-DIETDIET-NH2 (SEQ ID NO: 9), H-DIETDIETDIET-NH2 (SEQ ID NO: 8), and H-FDGDFDGD-NH2 (SEQ ID NO: 10).

2. A composition comprising a synthetic peptide consisting of a divalent cation binding site selected from the group consisting of H-DIET-NH2 (SEQ ID NO: 11), H-DIETDIET-NH2 (SEQ ID NO: 9), H-DIETDIETDIET-NH2 (SEQ ID NO: 8), and H-FDGDFDGD-NH2 (SEQ ID NO: 10), a thermostable DNA polymerase, a divalent cation, deoxynucleotides, and a buffer.

3. The composition according to claim 2 wherein the divalent cation is $Mg^{2+}$.

4. The composition according to claim 2 further comprising at least one nucleic acid compound.

5. A kit comprising a thermostable DNA polymerase and a synthetic peptide according to claim 1.

6. A method for amplification of a target nucleic acid comprising the steps of providing a sample suspected of containing the target nucleic acid, adding a composition according to claim 2, and performing a nucleic acid amplification reaction.

7. The method according to claim 6 wherein said nucleic acid amplification reaction is a polymerase chain reaction which is monitored in real time.

8. The method according to claim 6 further comprising the step of performing a melting curve analysis on an amplification product generated by the nucleic acid amplification reaction.

* * * * *

SEQUENCE LISTING

<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agacagtaca gccagcctca                                                  20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gacttcaaat ttctgctcct c                                                21

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agtatgcccc cgcacagga                                                   19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gggtgcatcg ggtgacctg                                                   19

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agccactgtg aggcggga                                                    18

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

-continued

```
caccccgtgc tgctgaccga                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agggaggcgg ccaccagaag                                               20

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Ile Glu Thr Asp Ile Glu Thr Asp Ile Glu Thr
 1               5                  10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Ile Glu Thr Asp Ile Glu Thr
 1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Phe Asp Gly Asp Phe Asp Gly Asp
 1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Ile Glu Thr
 1
```